United States Patent [19]

Pike

[11] 4,218,385
[45] Aug. 19, 1980

[54] TRI-SUBSTITUTED, HYDROCARBON SOLUBLE, CHROMIUM COMPOUND SYNTHESIS

[75] Inventor: Roscoe A. Pike, Simsbury, Conn.

[73] Assignee: United Technologies Corporation, Hartford, Conn.

[21] Appl. No.: 958,471

[22] Filed: Nov. 7, 1978

[51] Int. Cl.$^2$ .................... C09F 7/00; C11C 3/12; C11C 1/00
[52] U.S. Cl. .................... 260/408; 260/414; 260/438.5 C; 44/66; 44/68; 252/389 R
[58] Field of Search ............... 260/408, 414, 438.5 C

[56] References Cited

U.S. PATENT DOCUMENTS

| | | | |
|---|---|---|---|
| 3,185,717 | 5/1965 | Trebilcock | 260/438 |
| 3,256,266 | 6/1966 | Burt | 260/414 |
| 3,983,270 | 9/1976 | Licari et al. | 427/372 |
| 4,104,293 | 8/1978 | Redmore et al. | 260/414 |

FOREIGN PATENT DOCUMENTS 970494  9/1964  United Kingdom .

*Primary Examiner*—John F. Niebling
*Attorney, Agent, or Firm*—Harry J. Gwinnell

[57] ABSTRACT

An improved method for synthesizing a hydrocarbon soluble (RCOO)$_3$Cr chromium compound is described. The disclosed method employs a two-step reaction scheme utilizing a nonhalogenated chromium compound such as chromic acid anhydride as a starting material. In the first step the chromium source is reduced with an alcohol in the presence of a fatty acid to Cr$^{+3}$. The synthesis is completed by converting the reduced chromium to the tri-substituted compound by reaction with a fatty acid in the presence of a base. The chromium containing product has particular utility as a corrosion inhibiting fuel soluble additive.

5 Claims, 2 Drawing Figures

TRI-SUBSTITUTED, HYDROCARBON SOLUBLE, CHROMIUM COMPOUND SYNTHESIS

BACKGROUND OF THE INVENTION

1. Field of the Invention

The field of art to which this invention pertains is a method of synthesizing fatty acid compounds of chromium.

2. Description of the Prior Art

The advantages of the use of chromium compounds as fuel additives in such things as gas turbine engines to prevent corrosion has been well recognized in the prior art. Note U.S. Pat. No. 3,581,491. However, because of the numerous process steps required to make conventional reactants needed to produce these valuable complexes, the expense of conventional synthesis methods has been somewhat prohibitive. Specifically, chromium chloride ($CrCl_3$) has been conventionally used as the source of the chromium in conventional synthesis methods. This compound is not readily available but must be made and is therefore a relatively expensive starting material. Alternatively, other salts such as the sulfate ($Cr_2(SO_4)_3$) have been employed as the chromium source. However, from an availability and cost standpoint, little or no advantage is accomplished over the use of the chloride. Accordingly, what has been lacking in the prior art is a relatively simple method of producing chromium compounds useful e.g. as anticorrosion fuel soluble additives which utilize readily available and inexpensive chromium containing starting materials.

BRIEF SUMMARY OF THE INVENTION

According to the present invention, there is disclosed a relatively simple method of synthesizing trivalent, hydrocarbon soluble, fatty acid chromium compounds. The particular suitability of such compounds as fuel soluble additives to prevent corrosion in gas turbine engines is described. The described method utilizes readily available, relatively inexpensive reactant material, and particularly the chromium source, in such synthesis. Such synthesis is accomplished with no sacrifice in product performance or change in chemical or physical properties of the ultimate compound synthesized over conventionally used chromium containing fuel additives.

The foregoing and other objects, features and advantages of the present invention will become more apparent in light of the following detailed description of preferred embodiments thereof as discussed and illustrated in the accompanying drawing.

BRIEF DESCRIPTION OF THE DRAWINGS

The Figures demonstrate schematically preferred methods of synthesis.

DESCRIPTION OF THE PREFERRED EMBODIMENTS

Figure 1:
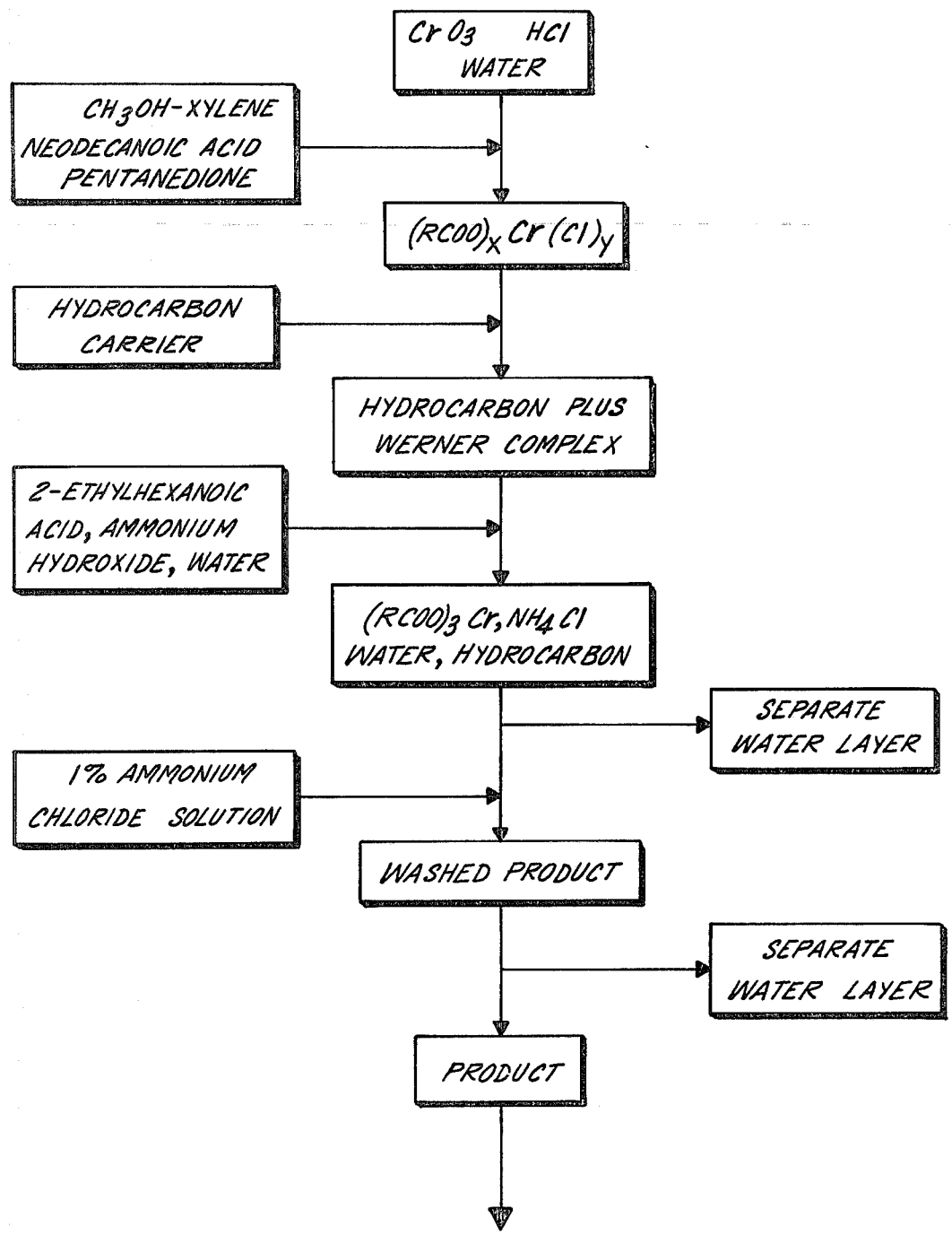

Conventionally, chromium-containing fatty acid compounds are formed by metathesis of an alkali metal salt of a fatty acid with a trivalent chromium salt, normally the chloride or sulfate. However, because of the many steps required to make such chromium containing materials, the cost of such reactants can be prohibitive for this purpose. It has been found that by utilizing a two-step synthesis, relatively available chromic acid anhydride ($CrO_3$) can be used as the chromium source in the production of such compounds. It has also been found that such compounds can be formed by such method with no sacrifice in product quality over conventional fuel soluble additives in spite of the relatively simple synthesis scheme.

The first stage in the synthesis comprises reducing the relatively toxic hexavalent chromium source to trivalent chromium by means of reducing agents such as alcohols. The course of reaction can be followed by absorption spectroscopy at typically either 440 or 510 millimicrons at which wavelength the trivalent chromium shows little or no absorption while the hexavalent chromium peak is strong. Such change in absorbance will indicate completion of the reduction step.

Preferably the reduction step is carried out in the presence of approximately one-third of the required stoichiometric amount of carboxylic acid required to form the tri-substituted chromium compound to prevent emulsion formation. The reaction is exemplified as follows:

(I)
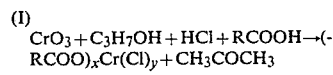
$$CrO_3 + C_3H_7OH + HCl + RCOOH \rightarrow (RCOO)_xCr(Cl)_y + CH_3COCH_3$$

wherein R is an aliphatic, alicyclic or branched hydrocarbon having at least 7 carbon atoms, $x+y=3$, and $y =$ at least 1. A similar reaction scheme is taught in U.S. Pat. No. 3,185,717 which discusses the best results with an excess of alcohol having a water solubility of at least 5% by weight. The patent also teaches that for uniformity of product the chromium compound and HCl should be added simultaneously. However, only the complexes are formed and there is no disclosure as to the ultimate fuel soluble soap formation.

The second phase of the improved process comprises completing the tri-substituted soap formation by reacting the required stoichiometric amount of carboxylic acid with the complex in the presence of a hydrocarbon carrier and a base to give the tri-substituted soap compound. While any carboxylic acid which is hydrocarbon soluble can be used, aliphatic carboxylic acids having at least 7 carbon atoms are preferred and 8 to 12 carbon atoms most preferred. Preferred hydrocarbons are kerosene, mineral spirits, No. 2 home heating oil and high flash point oil, with kerosene being most preferred. While any standard base such as sodium hydroxide or other alkali metal salt may be used, ammonium hydroxide is preferred because it produced no contaminating metal ions which must be removed for anti-corrosive fuel additive purposes. The concentration ranges of all the reactants are typified by the accompanying examples.

The second portion of the reaction scheme is exemplified as follows:

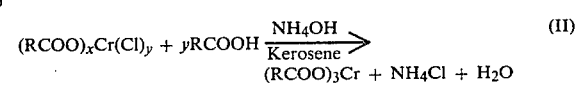
$$(RCOO)_xCr(Cl)_y + yRCOOH \xrightarrow[\text{Kerosene}]{NH_4OH} (RCOO)_3Cr + NH_4Cl + H_2O \quad (II)$$

where $x+y=3$, with y having a value of at least 1 and R is an aliphatic, alicyclic or branched carbon chain of at least 7 carbon atoms and preferably a $C_8$ to $C_{12}$ hydrocarbon.

Generally, enough hydrocarbon is employed to produce a 6.5–7% by weight chromium metal from the reaction product in the hydrocarbon. This value can, of course, be adjusted by the amount of hydrocarbon carrier used. After washing with a 1% by weight solution of ammonium chloride in water, the oil (hydrocarbon) layer can be used as produced for such purposes as a fuel additive in gas turbine engines to produce corrosion resistance. As stated above, part of the carboxylic acid making up the chromium complex is preferably added during the alcohol reduction step. The advantage of doing such is to prevent polymerization of the reaction mixture during formation of the chromium complex. It has also been found that addition of small amounts (up to 10 milliliters) of 2,4-pentanedione to the reaction mixture also has a polymerization prevention effect. This further contributes to viscosity control which can also be effected by the type of carboxylic acid used (the longer the carbon chain, the more viscous the final product) and the ratio of longer chain acids to shorter chain acids when a mixture of acids is used. Similarly, the amount of dione added will affect this viscosity.

As noted above, any aliphatic acid having at least 7 carbon atoms can be used with $C_8$ to $C_{12}$ aliphatic acids being preferred. It should also be noted that the type of acid used is not limited to only one acid but a mixture of acids may also be used with such considerations as viscosity of the final product and costs of the acids employed being the determinative factor. Also, the same acid does not have to be used in the reduction and soap formation steps. Note the Examples. Acids such as 2-ethylhexanoic, octanoic and pelargonic are preferred, neodecanoic and naphthenic most preferred. When using naphthenic acid, replacement of part of the preferred methanol reducing alcohol with isopropyl alcohol is necessary to prevent intermediate Werner complex insolubility and emulsion formation (note Example 3). The viscosity of the final product is also higher using naphthenic acid as opposed to neodecanoic acid since the acid itself has a higher viscosity than neodecanoic acid. A combination of two or more of the branched chain or aliphatic acids can be used to maintain control of the final viscosity of the reaction mixture at the chromium content desired. The most preferred admixture is comprised of neodecanoic and 2-ethylhexanoic carboxylic acids.

Washing the final product with a 1% ammonium chloride solution will produce two beneficial effects, (1) removal of unreacted materials, and (2) alleviation of emulsion formation of the oil and water phases when removing the reaction product, resulting in good oil-water separation.

As the reducing alcohol any alcohol with at least 5% solubility in water can be used. Methyl and isopropyl alcohols are preferred with the most preferred alcohol in the reduction step being methyl alcohol. And if desired, methyl alcohol containing 5% xylene can be used for cost saving purposes.

An essential part of the reaction scheme is the use of at least a 7.5 times the amount of alcohol necessary to reduce the $Cr^{+6}$ to $Cr^{+3}$ in the initial complex formation reduction step. With less than this amount the intermediate Werner complex formed (see reaction scheme I) insolubilizes, adversely affecting the remainder of the reaction and attainable yields. Also, emulsion formation will take place in the washing step due to the molecular weight of the soap micelles which are formed during reaction. The greater the dilution, the lower the micelle molecular weight, causing less tendency to absorb water and cause emulsification.

Some exemplary dilutions are demonstrated in Table I with the corresponding viscosity and percent chromium measurements resulting from such addition. This has particular utility when the ultimate chromium product is to be used as a fuel additive for anticorrosion purposes, for example in gas turbine engines where different user specifications can be modified at this reduction step. Preferably the viscosity of the chromium compound-hydrocarbon composition upon completion of the two-stage reaction will be less than 500 cs with 100–150 cs most preferred, and the chromium metal content in the hydrocarbon from the chromium compound formed will be between 5 and 8% by weight with 7% most preferred. Table II further demonstrates preferred standards for the composition in this utility.

TABLE I

| Amount of Alcohol | Reduction Step Addn. | Soap Formation Addn.[a] | Viscosity, cs | % Cr |
|---|---|---|---|---|
| 10× | alcohol to chromic acid | as solution | 102 | 6.9 |
| 10× | chromic acid to alcohol | consecutively | 66.4 | 7.1 |
| 7.5× | chromic acid to alcohol | as solution | 96 | 7.0 |
| 7.5× | chromic acid to alcohol | consecutively | 121.5 | 7.2 |
| 7.5× | chromic acid to alcohol[b] | consecutively | 170 | 6.73 |

[a]Addition of water, 2-ethyl hexanoic acid and $NH_4OH$.
[b]Naphthenic acid in place of neodecanoic acid with combination of methyl and isopropyl alcohol.

TABLE II

| | |
|---|---|
| Chromium content | 7 percent ± 0.1 percent |
| Kinematic viscosity | 500 centistokes, maximum at 70° F. |
| Flash point (Penske Martin Closed Cup) | 150° F. minimum |
| Sodium and potassium content | 0.02 percent maximum |

It has been shown both from a safety standpoint (no large rapid exotherm) and a shorter overall reaction time that the addition of the chromic-hydrochloric acid solution to the alcohol-fatty acid solution is the preferred method of carrying out the reduction step. This not only results in a much more controllable reaction but allows addition of a small volume of material to a large volume rather than the reverse. Since the chromic acid is always added to a large excess of alcohol, the reduction proceeds at a more rapid rate and the boiling point of the alcohol controls the upper temperature of the reaction at the reflux temperature. The reduction step is easily followed by measuring the UV transmission of the solution at 440 m$\mu$. The initial chromic acid solution has a UV transmission of 13 percent prior to addition to the alcohol. The transmission increases to 93 percent maximum at the end of the reduction indicating all the $Cr^{+6}$ has been reduced to $Cr^{+3}$. The dependence of the rate of reduction on the mode of addition is easily seen. Addition of the chromic acid to the alcohol results in more rapid reduction of $Cr^{+6}$ to $Cr^{+3}$.

It is preferred to premix the $CrO_3$, water and hydrochloric acid prior to addition to the alcohol. All other materials can be added without prior mixing. Typical reaction runs are described by the following Examples.

EXAMPLE 1

The following procedure describes the runs carried out on a 22 liter scale.

To a 22 liter fluted side round bottom flask having a drain plug on the bottom equipped with mechanical stirrer, dropping funnel, thermometer and reflux condenser was charged 240 g CrO₃, 150 cc water and 105 g of concentrated hydrochloric acid. The acid and CrO₃ were added simultaneously in five portions. To the resulting solution, with stirring, was slowly added a solution consisting of 2250 g methanol, 112.5 g xylene, 330 g neodecanoic acid and 60 g of 2,4-pendanedione. An exotherm occurred raising the temperature to 50° C. The rate of addition was controlled so that the temperature did not raise above 50° C. After approximately 20 percent of the solution had been added, no further exotherm occurred and the remainder of the solution was added while maintaining the temperature at 50°–55° C. using a heating mantel. Time of addition was 3 hours. After the addition was complete, the temperature was maintained at 60°–65° C. for 2 hours. A green-blue color indicated completion of the reduction. A trace of gummy solid was noted on the sides of the flask indicating a small amount of polymerization or Werner complex insolubility had occurred. Without the 2,4-pentanedione present, copious amounts of such a compound are formed. To the blue-green solution was then added 1050 cc of kerosene. Any gum formed in the reduction step dissolved in the hydrocarbon. A solution of 2400 cc water, 600 g concentrated ammonium hydroxide and 780 g of 2-ethylhexanoic acid was then added at such a rate as to maintain the temperature at 60°–65° C. with heating. After the addition was complete the reaction mixture was stirred 2 hours at 60°–65° C. The stirring was then stopped and the resulting water layer (bottom) separated. The blue-green oil layer was washed with 6 liters of a 1 percent ammonium chloride solution by stirring at 55° C. one-half hour. The resulting water layer was separated and the oil layer collected to give 2100 cc of product, 1950 g, having a Cr metal content of 6.51 percent, viscosity 92.5 Cs (25° C.) and a density of 0.93 g/cc. Analysis showed the product contained 2.5 ppm Cl, 6 ppm Pb and 1.3 ppm Na.

The soap component produced will have the formula:

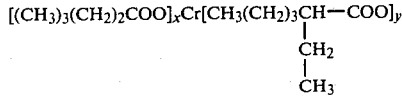

where x+y=3 and y=at least 1. A flow diagram of the process is shown in FIG. 1.

EXAMPLE 2

The following describes a run carried out on a 1 liter scale.

To a 1 liter-3-necked round bottom flask, having a drain plug on the bottom, equipped with a mechanical stirrer, thermometer, reflux condenser, and dropping funnel was charged 112.5 g methyl alcohol, 5.5 g xylene, 22 g neodecanoic acid and 4 g of 2,4-pentane dione. Through the dropping funnel was added dropwise with stirring a solution of 10 g of water, 16 g CrO₃ and 14 g of conc. hydrochloric acid over a 20 minute period. After 10 minutes the temperature had risen to 50° C. and in 15 minutes to 60° C. At the completion of the addition the UV transmission at 440 mμ was 81%. The solution was heated an additional 40 minutes (UV transmission at 440 mμ=93%) at 60°–65° C. To the dark green solution, with stirring, was then added in consecutive order 55.5 g (70 cc) of kerosene, 100 g water and 52 g of 2-ethyl hexanoic acid. During these additions the temperature dropped to 50° C. Through the dropping funnel was then added 31 g of conc. ammonium hydroxide over a 10 minute period, the temperature rose to 62° C. The resulting mixture was stirred at 60°–61° C. for ¾ hour. The stirrer was stopped and the layers allowed to separate over a fifteen minute period. The bottom aqueous layer which was drawn off had a pH of 7.5 and amounted to 325 cc. To the purple oil layer was then added 325 cc of 1% NH₄Cl solution with stirring. The temperature dropped to 40° C. The mixture was heated to 50° C. and stirred ½ hr. After phase separation for 15 minutes the wash water was drawn off and the product collected. The weight of the product was 123 g, viscosity 120 cs and Cr content 7.2%.

Figure 2:
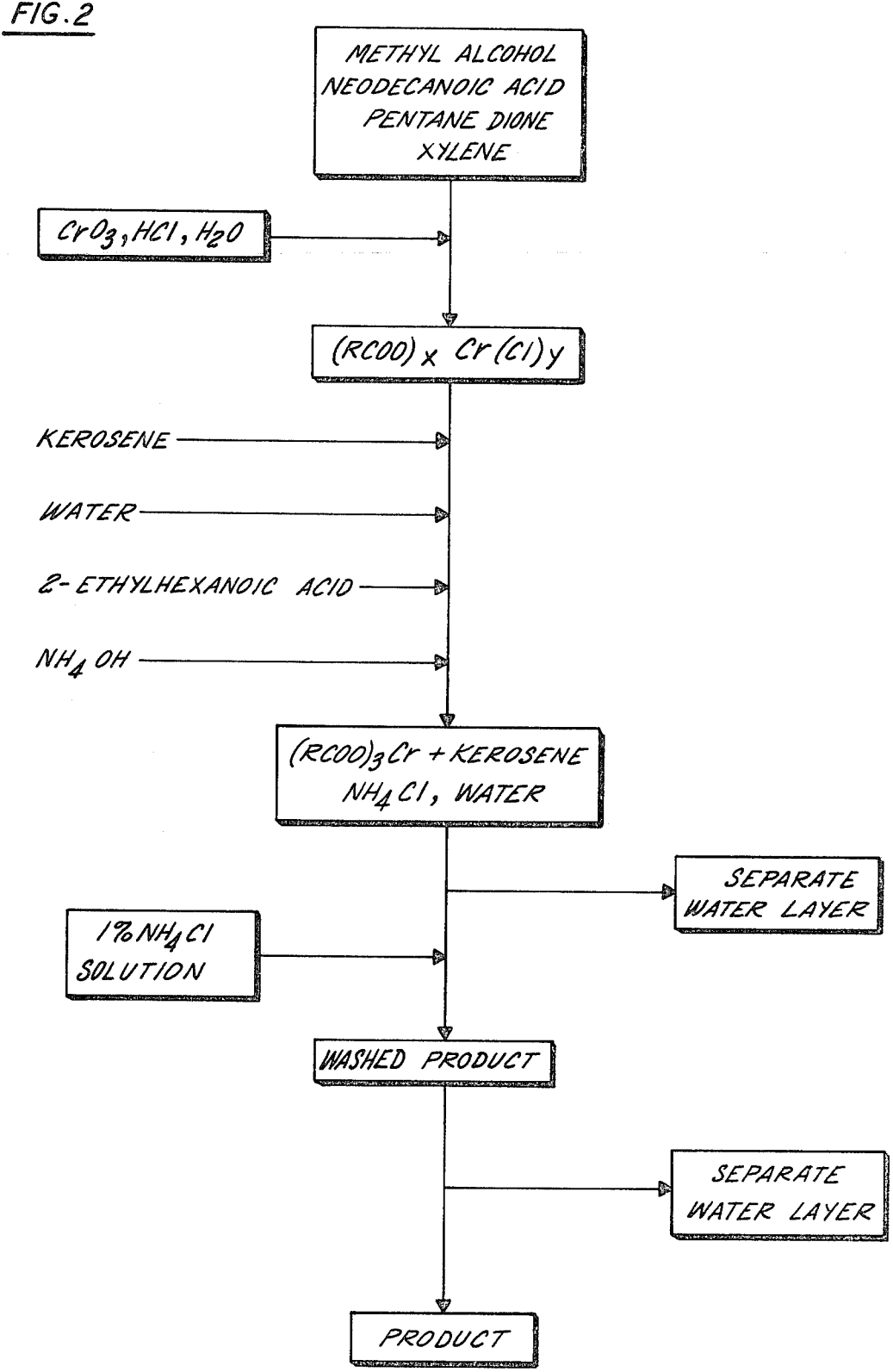

A flow diagram of the process is shown by FIG. 2.

EXAMPLE 3

The procedure of Example 2 was carried out using naphthenic acid (22 g.) in place of neodecanoic acid during the reduction step. The only change which was made was that isopropyl alcohol was used together with methyl alcohol to insure solubility of the Werner complex and prevent emulsion formation. Thus 75 g. of methyl alcohol and 37.5 g. of isopropyl alcohol, totaling 112.5 g., were used to give 122 g. of product with a viscosity of 170 cs, and a Cr content of 6.73%.

Having thus described typical embodiments of my invention, that which I claim as new and desire to secure by Letters Patent of the United States is:

1. A process of forming a kerosene solution of a hydrocarbon soluble, trivalent chromium, fatty acid compound particularly adapted to perform as an anticorrosive fuel soluble additive, comprising reacting CrO₃, concentrated HCl, methanol, isopropanol and naphthenic acid in water containing 2,4-pentanedione thereby forming a Werner complex of the acid, chromium, and HCl supplied chloride, the methanol and isopropanol being present in an amount at least 7.5 times that necessary to reduce the CrO₃, and the naphthenic acid being present in an amount about one-third the stoichiometric amount of fatty acid necessary to form the trivalent chromium compound, adding kerosene to the complex containing composition, adding more water, concentrated ammonium hydroxide and 2-ethylhexanoic acid to the composition to react with the complex thereby forming a trivalent chromium fatty acid compound dissolved in the added kerosene, separating the water from the composition, and washing the resulting kerosene layer with a one percent solution of ammonium chloride resulting in a kerosene solution of the chromium compound having a chromium metal content of about 5 to 8% and a viscosity less than 500 cs.

2. A process of forming a kerosene solution of a hydrocarbon soluble, trivalent chromium, fatty acid compound particularly adapted to perform as an anticorrosive fuel soluble additive, comprising reacting CrO₃, concentrated HCl, methanol and neodecanoic acid in water containing 2,4-pentanedione thereby forming a [(CH₃)₃(CH₂)₆COO]ₓCrCl_y Werner complex where x+y=3 and y=at least 1, the methanol being present in an amount at least 7.5 times that necessary to reduce the CrO₃, and the neodecanoic acid being present in an amount about one-third the stoichiometric amount of fatty acid necessary to form the trivalent chromium compound, adding kerosene to the complex containing composition, adding more water, concentrated ammonium hydroxide and 2-ethylhexanoic acid to the composition to react with the complex thereby forming a chromium containing compound of the formula

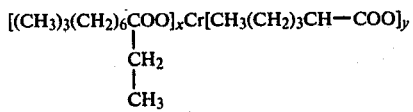

dissolved in the added kerosene where x and y are defined as above, separating the water from the composition, and washing the resulting kerosene layer with a 1% solution of ammonium chloride resulting in a kerosene solution of the chromium compound having a chromium metal content of about 5 to 8% and a viscosity less than 500 cs.

3. The process of claim 2 wherein the methanol used contains 5% by weight xylene.

4. The process of claim 1 wherein the methanol used contains 5% by weight xylene.

5. The process of claim 1 or 2 wherein 2,4-pentanedione is added to the reaction mixture after the formation of the Werner complex.

* * * * *